United States Patent [19]

Buzby, Jr.

[11] Patent Number: 4,587,360

[45] Date of Patent: * May 6, 1986

[54] ANTI-ARRHYTHMIC AGENTS

[75] Inventor: George C. Buzby, Jr., Blue Bell, Pa.

[73] Assignee: American Home Products Corporation, New York, N.Y.

[*] Notice: The portion of the term of this patent subsequent to Sep. 3, 2002 has been disclaimed.

[21] Appl. No.: 723,685

[22] Filed: Apr. 16, 1985

Related U.S. Application Data

[63] Continuation-in-part of Ser. No. 717,739, Mar. 29, 1985, abandoned, which is a continuation-in-part of Ser. No. 609,151, May 11, 1984, Pat. No. 4,539,426.

[51] Int. Cl.$^4$ .................. C07C 143/72; C07C 143/78; C07C 143/80
[52] U.S. Cl. ...................... 564/92; 514/604; 514/603; 514/523
[58] Field of Search .......................................... 564/92

[56] References Cited

U.S. PATENT DOCUMENTS

| | | | |
|---|---|---|---|
| 3,546,204 | 12/1970 | Weaver et al. | 564/92 X |
| 4,013,621 | 3/1977 | Knell | 524/92 X |
| 4,233,061 | 11/1980 | Takematsu et al. | 564/92 X |
| 4,401,666 | 8/1983 | Buckwalter et al. | 564/92 X |

FOREIGN PATENT DOCUMENTS

| | | | |
|---|---|---|---|
| 24229 | 3/1975 | Japan | 564/92 |
| 2119378 | 11/1983 | United Kingdom | 564/92 |

OTHER PUBLICATIONS

Fleckenstein, Ann. Rev. Pharmacol, 17, 149–166 (1977).

*Primary Examiner*—Paul F. Shaver
*Attorney, Agent, or Firm*—Richard K. Jackson

[57] ABSTRACT

An anti-arrhythmic agent which is N-[3-[[2-(3,4-dimethoxyphenyl)ethyl]methylamino]propyl]-N-(1-methylethyl)-2,3,4-trimethoxy-benzenesulfonamide or a pharmaceutically acceptable salt thereof.

1 Claim, No Drawings

4,587,360

ANTI-ARRHYTHMIC AGENTS

This is a continuation-in-part of U.S. patent application Ser. No. 717,739, filed Mar. 29, 1985, now abandoned, which is a continuation-in-part of U.S. patent application Ser. No. 609,151, filed May 11, 1984, now U.S. Pat. No. 4,539,426 by George C. Buzby, Jr., entitled Anti-Arrhythmic Agents.

BACKGROUND OF THE INVENTION

Pharmacological agents possessing the ability to block cellular transmembrane influx of calcium are capable of suppressing that portion of myocardial or vascular smooth muscle contractility which is dependent upon extracellular calcium. Church et al., Can. J. Physiol. Pharmacol., 58, 254 (1980); Fleckenstein, Calcium and the Heart, P. Harris and L. Opie, eds., Academic Press (1971); Nayler et al., Bas. Res. Cardiol., 76, 1 (1981); Calcium Blockers, S. Flaim and R. Zelis, eds., Urban and Schwartzenberg, (1982).

These pharmacological agents, termed calcium entry blockers, have been proven to be useful in the treatment of hypertension, cardiac arrhythmias, angina pectoris, and coronary artery vasospasm (a possible cause of sudden cardiac death syndrome). Circ. Res., 52, Suppl. I, (1983); Hypertension 5, Suppl. II, (1983). In theory, calcium entry blockers are thought to act by blocking calcium influx through discrete calcium channels (slow channels) in cell membranes. Various tissues exhibit relative differences in sensitivity toward the calcium blocking effect achieved by certain calcium antagonists, theoretically as a result of tissue specific differences in the calcium channels. Acta Pharmacol. Toxicol., 43, 5 (1978); loc. cit. 291 (1978); Microvascular Res., 5, 73 (1973); Am. Rev. Pharmacol. Toxicol., 17, 149 (1977). It is believed that the slow calcium current is responsible for activation of pacemaker cells in the sinoatrial node and the atrioventricular node of the heart. Verapamil, a known calcium channel blocking agent, is believed to slow conduction velocity through the atrio-ventricular node of the heart, in explanation of the mechanism of its anti-arrhythmic activity.

DESCRIPTION OF THE INVENTION

In accordance with this invention there is provided a group of compounds of the formula:

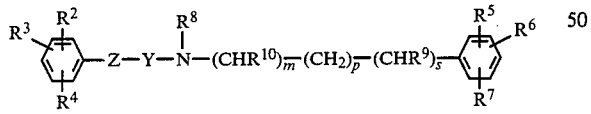

in which
Y is $-(CH_2)_n-$ where n is one of the integers 1, 2, 3 or 4 or

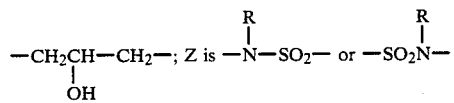

where R is hydrogen, alkyl of 1–6 carbon atoms, polyfluorinated alkyl of 1 to 6 carbon atoms, —CN, cyanoalkyl in which the alkyl moiety contains 1 to 3 carbon atoms, cycloalkyl of 3 to 6 carbon atoms or cycloalkylalkyl of 4 to 8 carbon atoms;

$R^2$, $R^3$, $R^4$, $R^5$, $R^6$ and $R^7$, independently, are hydrogen, alkoxy of 1–3 carbon atoms, trifluoromethyl, —Cl, —Br or —F;
$R^8$ is hydrogen or alkyl of 1 to 6 carbon atoms;
$R^9$ is alkyl of 1 to 3 carbon atoms;
$R^{10}$ is alkyl of 1 to 3 carbon atoms;
m is one of the integers 0 or 1;
p is one of the integers 0, 1, 2 or 3; and
s is one of the integers 0 or 1;
or a pharmaceutically acceptable salt thereof, with the provisos that the sum of m, p and s must be 1, 2, 3 or 4; and the number of linear atoms in the bridge connecting the two aromatic rings does not exceed 8; and when n is 1 or 2, two of $R^2$, $R^3$ and $R^4$ are other than hydrogen.

With reference to the above-described genus of compounds, the preferred variables from the standpoint of production economics and activity profile may be grouped as those in which (1) the aromatic ring to the left of the depicted structure contains three substituents in 3-, 4- and 5-positions where, preferably those substituents are lower alkoxy (most preferably methoxy), Y is trimethylene, m and s are 0 and p is 2; (2) the aromatic ring to the left of the depicted structure contains two substituents, either in the 3,5- or 3,4-positions, where preferably those substituents are lower alkoxy (most preferably methoxy) or halo (most preferably —Cl), Y is di- or tri-methylene, m and s are 0 and p is 2; and (3) the aromatic ring to the left of the depicted structure contains one substituent, in meta position, Y is trimethylene, m and s are 0 and p is 2.

The pharmaceutically acceptable salts of the anti-arrhythmic agents of this invention are prepared directly by neutralization of the free base or by metathetical displacement. The physiologically acceptable salts may be formed with organic or inorganic acids such as hydrochloric, hydrobromic, phosphoric, sulfuric, sulfonic, nitric, methylsulfonic, acetic, maleic, succinic, fumaric, tartaric, citric, salicylic, lactic, naphthalenesulfonic acid, and the like.

The compounds of this invention are prepared by several stage processes involving alkylation reactions performed on amines or sulfonamides or both. Briefly, an appropriately substituted aromatic amine

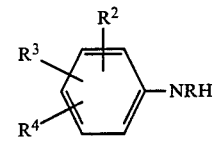

in which $R^2$, $R^3$, $R^4$ and R are as defined above, is reacted with $ClSO_2-Y-Cl$ wherein Y is as defined above, and the product is employed to alkylate an aralkylamine of the formula

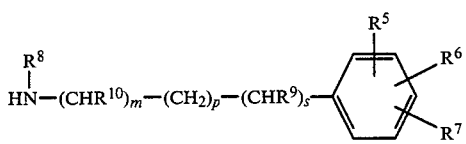

where $R^{5-10}$, m, p and s are as defined, supra. This reaction sequence affords the N-aromatic-propanesulfonamide type compounds of this series. The benzenesulfonamide type compounds of this series are produced in analogous manner by reaction of an appropriately substituted aromatic sulfonamide

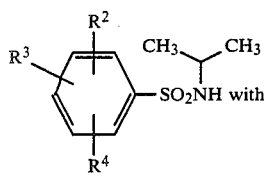

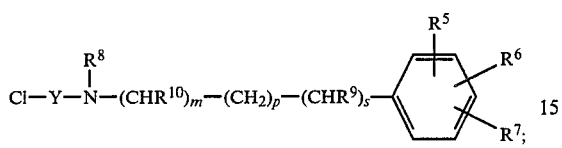

or by reaction of an aromatic sulfonyl halide with an omegahydroxy alkylamine followed by N-alkylation and replacement of the hydroxyl group with a halogen, and alkylation of the appropriate aralkylamine. The intermediates employed are either known compounds or are prepared from literature compounds by procedures well within the skill of the medicinal chemist.

The compounds of this invention exhibit $Ca^{+2}$ antagonism in rabbit aortic smooth muscle when tested by a modified procedure from that described by Brockaert et al., Eur. J. Pharmacol., 53, 281 (1979). Here, transverse strips (10 mm×2.5 mm) from the thoracic aorta were cut and suspended vertically in a jacketed (37° C.-50 ml volume) organ bath in physiological saline solution (PSS) aerated with 95% $O_2$/5% $CO_2$. The composition of PSS was as follows (mM): NaCl 112, KCl 5, $NaHCO_3$ 25, $KH_2PO_4$ 1, $MgSO_4$ 1.2, $CaCl_2$ 2.5, dextrose 10. The lower end of each tissue strip was attached to a fixed post and the upper end to a Statham UC-4 transducer. Changes in force development were recorded on a Beckman Dynograph Polygraphic Recorder.

Following equilibration, the muscles were contracted in a depolarizing solution of PSS in which 100 mM KCl was substituted for an equimolar concentration of NaCl. Following attainment of steady-state isometric force (20 min.), the test compound was added to afford a final concentration of $1 \times 10^{-5}M$. The inhibitory effect, expressed as percent relaxation, was determined from the mean of two experiments twenty minutes after the addition of the compound being tested.

In addition, the compounds of this invention demonstrate an inhibitory influence on arterial $Ca^{+2}$-calmodulin dependent myosin light chain phosphorylation and subsequent contractile protein function when tested in standard experimental procedures for these inhibitory properties.

As such, the compounds of the invention present an activity profile consistent with that of anti-arrhythmic agents, which utility was proven by in vivo experiments in the standard experimental animal as follows:

Rats weighing between 400-500 gms were anesthetized with 35-40 mg/kg Na pentobarbital i.p. Rats were close-clipped on the neck and left side prior to cannulation of the jugular vein and tracheotomy. In some experiments, a catheter was introduced into the carotid artery for measurement of arterial blood pressure. Respiration was provided by a Harvard Model 681 respirator at a rate of approximately 55/min and a volume of 4 cc per cycle. The rat was then placed upon its right side and the heart was exposed by making an incision and separating the ribs. 4-0 silk on taper RB-1 needle was passed under the left anterior descending coronary artery (LAD) at a location just under the tip of the left atrial appendage. The suture was left to be tied upon occlusion. Lead II ECG and cardiotachometer output were recorded on a Beckman R612.

The rat was allowed to stabilize for several minutes before the administration (1 mg/kg) of drug via the cannulated jugular vein. Compounds were suspended in carbowax, with total dose volumes kept below 0.20-0.25 ml. Fifteen minutes after dosing, the LAD was occluded by tying the suture. This procedure provokes severe ventricular arrhythmias, terminating in ventricular fibrillation and death in approximately 73 percent of animals given vehicle only. Data were analyzed based on statistical analysis of heart rate fluctuations. Output from a Beckman cardiotachometer was digitized at 200 msec/pt using a Nicolet 3091 digital oscilloscope, and the data analyzed to yield mean ± variance of the rate for each 1 minute period (300 points). The measured variance for the period 5-11 minutes post-occlusion was well correlated with the severity of the observed ventricular arrhythmias, and provided a quantitative measure for the relative antiarrhythmic effectiveness of the compound being tested.

For the purpose of these coronary ligation (C.L.) experiments, the actual mortality rate, expressed as a percentage of the animals employed, was obtained for purpose of comparison with the mortality rate of 73 percent in vehicle-treated animals.

Thus, these data establish the compounds of this invention as $Ca^{+2}$ antagonists which are useful as antiarrhythmic agents functioning more at the vascular level than other known $Ca^{+2}$ entry blockers. It has been observed that compounds of this invention inhibit arterial $Ca^{+2}$-calmodulin dependent myosin light chain phosphorylation and subsequent contractile protein function.

Based upon the activity profile elicited by the compounds of this invention in the above-described standard scientifically recognized test models, the compounds are established as anti-arrhythmic agents useful in the treatment of cardiac arrhythmias and conditions characterized by coronary arteries vasospasm. For that purpose, the compounds may be administered orally or parenterally in suitable dosage forms compatable with the route of administration, whether oral, intraperitoneal, intramuscular, intravenous, intranasal, buccal, etc. The effective dose range determined in the animal test models has been established at from 1 to about 50 milligrams per kilogram host body weight to be administered in single or plural doses as needed to relieve the arrhythmatic dysfunction. The specific dosage regimen for a given patient will depend upon age, pathological state, severity of dysfunction, size of the patient, etc. Oral administration is performed with either a liquid or solid dosage unit in any conventional form such as tablets, capsules, solutions, etc., which comprise a unit dose (e.g. from about 25 milligrams to about 4 grams) of the active ingredient alone or in combination with adjuvants needed for conventional coating, tableting, solubilizing, flavoring or coloring. Parenteral administration with liquid unit dosage forms may be via sterile solutions or suspensions in aqueous or oleagenous medium. Isotonic aqueous vehicle for injection is preferred with or without stabilizers, preservatives and emulsifiers.

The following examples illustrate the preparation of a representative number of compounds of this invention.

After each example, the Ca$^{+2}$ antagonist activity of the compound is presented in terms of percent relaxation (P.R.) at $10^{-5}$M concentration unless indicated otherwise. Similarly, the percentage mortality of standard experimental test animals upon coronary ligation (C.L.) is presented for comparison with the control mortality rate of 73 percent of animals receiving vehicle alone.

EXAMPLE 1

N-(3,5-Dimethoxyphenyl)-3-[[2-(3,4-dimethoxyphenyl)ethyl]methylamino]-N-(1-methylethyl)-1-propanesulfonamide 3,5-Dimethoxyaniline (34.62 g, 0.226 mol) in xylene (500 mL) containing suspended sodium carbonate (12.0 g, 0.113 mol) was treated with 3-chloropropane sulfonyl chloride (40.0 g, 0.226 mol) added dropwise with stirring. Stirring was continued for twenty-four hours and the solvent was stripped to provide a black partially crystalline gum. Filtration through dry-column silica gel combined with crystallization from ethyl acetate/hexane provided N-(3,5-dimethoxyphenyl)-3-chloro-1-propanesulfonamide (20 g), m.p. 68°–71° C.

N-(3,5-Dimethoxyphenyl)-3-chloro-1-propanesulfonamide prepared in the preceding paragraph (16.56 g, 0.057 mol) was dissolved in xylene (300 mL) containing potassium carbonate (7.86 g, 0.057 mol) and N-methylhomoveratrylamine (11.13 g, 0.057 mol) and the reaction warmed and stirred three days. Filtration, stripping of solvent and chromatography on dry-column silica gel (1100 g) with 5% methanol/ethyl acetate provided crude N-(3,5-dimethoxyphenyl)-3-[[2-(3,4-dimethoxyphenyl)ethyl]methylamino]-1-propanesulfonamide (5.32 g).

The product of the preceding paragraph (2.49 g, 0.0055 mol) in dry dimethylformamide (70 mL) was treated with sodium hydride (60% in mineral oil) (0.22 g, 0.0055 mol) and the reaction was stirred for one hour. Isopropyl bromide (0.677 g, 0.0055 mol) was added and the solution stirred overnight. The reaction was stripped and chromatography provided the title product (0.43 g) as a gum containing a trace of methylene chloride.

Analysis for: $C_{25}H_{38}SO_6N_2.0.2CH_2Cl_2$: Calculated: C, 59.16; H, 7.56; N, 5.47. Found: C, 59.26; H, 7.59; N, 5.39.

P.R.=90 at $10^{-5}$M; 27 at $10^{-6}$M.
C.L.=50%.

EXAMPLE 2

N-(3,4-Dimethoxyphenyl)-3-[[2-(3,4-dimethoxyphenyl)ethyl]methylamino]-N-(1-methylethyl)-1-propanesulfonamide The title compound was prepared by the method of the preceding Example with the exception that 3,4-dimethoxyaniline rather than 3,5-dimethoxyaniline was employed as the starting material.

Analysis for: $C_{25}H_{38}SO_6N_2$: Calculated: C, 60.70; H, 7.74; N, 5.66. Found: C, 60.39; H, 7.96; N, 5.67.

P.R.=74.
C.L.=0%.

EXAMPLE 3

3-[[2-(3,4-Dimethoxyphenyl)ethyl]methylamino]-N-(1-methylethyl)-N-(3,4,5-trimethoxyphenyl)-1-propanesulfonamide 3,4,5-Trimethoxyaniline (38.3 g, 0.208 mol) in xylene (800 mL), containing a small amount of methylene chloride to maintain a solution, was treated with sodium carbonate (22.13 g). Then 3-chloropropanesulfonylchloride (36.95 g) was added dropwise with stirring and stirring was continued overnight at room temperature. Cooling, filtration and evaporation provided a semisolid mass which was triturated with diethyl ether, filtered and the filtrate taken to dryness. Chromatography of the residue obtained from the filtrate on dry-column silica gel with 50—50 ethyl acetate/hexane provided by trituration with diethyl ether N-3,4,5-trimethoxyphenyl-3-chloro-1-propanesulfonamide (13.09 g) m.p. 84°–85° C.

N-3,4,5-Trimethoxyphenyl-3-chloro-1-propanesulfonamide (13.06 g, 0.04 mol) in xylene (300 mL), sodium carbonate (3.18 g, 0.03 mol), cesium carbonate (3.25 g, 0.01 mol) and N-methylhomoveratrylamine (7.88 g, 0.04 mol) were heated together with stirring for four days. Cooling, filtering and stripping provided a crude product (21.60 g) which was triturated with diethyl ether and filtered. Chromatography on alumna with 4% methanol/ethyl acetate provided 3-[[2-(3,4-dimethoxyphenyl)ethyl]methylamino]-N-(3,4,5-trimethoxyphenyl)-1-propanesulfonamide (6.0 g) as a gum, containing traces of dimethylformamide and ethyl acetate.

3-[[2-(3,4-Dimethoxyphenyl)ethyl]methylamino]-N-(3,4,5-trimethoxyphenyl)-1-propanesulfonamide (6.7 g, 0.0139 mol) in dry dimethylformamide (100 mL) was treated with sodium hydride, 60% in mineral oil, (0.555 g, 0.0139 mol) and the reaction stirred 1 hour at which point 2-bromopropane (1.71 g, 0.0139 mol) was added and the solution warmed overnight. The reaction was then stripped, dissolved in methylene chloride, filtered and evaporated to a gum. Preparative high pressure chromatography provided the title compound (3.40 g).

Analysis for: $C_{26}H_{40}N_2O_7S$: Calculated: C, 59.52; H, 7.68; N, 5.34. Found: C, 58.76; H, 7.73; N, 5.34.

P.R.=62.
C.L.=8.3%.

A portion of the product of the preceding paragraph was crystallized from diethyl ether to provide a crystalline solid m.p. 65°–67° C.

EXAMPLE 4

N-(3,5-Dichlorophenyl)-3-[[2-(3,4-dimethoxyphenyl)ethyl]methylamino]-N-(1-methylethyl)-1-propanesulfonamide The title compound was prepared from 3,5-dichloroaniline, following the procedures of the preceding examples.

Analysis for: $C_{23}H_{32}N_2O_4SCl_2$: Calculated: C, 54.87; H, 6.41; N, 5.56. Found: C, 55.02; H, 6.24; N, 5.48.

P.R.=86.
C.L.=0%.

EXAMPLE 5

N-(3-Trifluoromethylphenyl)-3-[[2-(3,4-dimethoxyphenyl)ethyl]methylamino]-1-propanesulfonamide This compound was prepared from 3-trifluoromethylaniline by the preceding method.

Analysis for: $C_{21}H_{27}N_2O_4SF_3$: Calculated: C, 54.77; H, 5.91; N, 6.08. Found: C, 54.57; H, 5.58; N, 5.85.

P.R.=51.
C.L.=25%.

EXAMPLE 6

N-(3-Trifluoromethylphenyl)-3-[[2-(3,4-dimethoxyphenyl)ethyl]methylamino]-N-(1-methylethyl)-1-propanesulfonamide This material was prepared from the substance described in the preceding example by alkylation as in Example 3 and purified by chromatography. $^1$H NMR (CDCl$_3$) −1.12 (d, 6, J=3.5 Hz Me$_2$) 2.30 (s, 3, —N—Me) 3.84 (d, 6, (OMe)$_2$) 6.72 (m, 3, aryl), 7.56 (m, 4, aryl).

Analysis for: C$_{24}$H$_{33}$N$_2$O$_4$SF$_3$: Calculated: C, 57.36; H, 6.62; N, 5.57. Found: C, 57.16; H, 6.67; N, 5.51.
P.R.=78.5.
C.L.=14%.

EXAMPLE 7

N-[3-[[2-(3,4-Dimethoxyphenyl)ethyl]methylamino]propyl]-N-(1-methylethyl)-3-(trifluoromethyl)benzenesulfonamide N-isopropyl-3-trifluoromethylbenzenesulfonamide (5.362 g, 0.02 mol) in dimethylformamide (30 mL) was treated with sodium hydride (60% in mineral oil), (0.802 g) and stirred for 2 hours. Then N-(3-chloropropyl)-3,4-dimethoxy-N-methylphenethylamine (5.436 g, 0.02 mol) was added and the reaction heated overnight. Filtration and removal of solvent provided the crude product (6.95 g). Column chromatography and high pressure liquid chromatography provided the pure product (4.35 g) as a gum. $^1$H NMR (CDCl$_3$) 1.15 (d, 6, J=3.5H, Me$_2$) 2.25 (s, 3, N-Me) 3.84 (d, 6, (OMe)$_2$) 6.76 (m, 3, Ar) 7.25 (m, 3, Ar).

Analysis for: C$_{24}$H$_{33}$N$_2$O$_4$SF$_3$: Calculated: C, 57.36; H, 6.62; N, 5.57. Found: C, 57.44; H, 6.66; N, 5.48.
P.R.=86.6.
C.L.=33%.

EXAMPLE 8

N-[3-[[2-(3,4-Dimethoxyphenyl)ethyl]methylamino]propyl]-N-(1-methylethyl)-3-(trifluoromethyl)benzenesulfonamide N-(3-chloropropyl)-N-(1-methylethyl)-3-trifluoromethylbenzenesulfonamide (23.4 g, 0.068 mol) and N-methylhomoveratrylamine (13.29 g, 0.068 mol) in xylene (250 mL) containing anhydrous potassium carbonate (4.68 g, 0.034 mol) and cesium carbonate (11.08 g, 0.034 mol) were heated and stirred for 2½ days. The reaction was cooled, filtered and stripped to provide a gum with a small amount of crystalline material evident. Solution in diethyl ether, filtration of the small amount of solid and concentration of the filtrate provided the crude product (32.91 g). Chromatography first on dry column alumina then silica gel provided the same product as in the preceding example (11.84 g) as a gum.

EXAMPLE 9

N-[3-[[2-(3,4-Dimethoxyphenyl)ethyl]methylamino]propyl]-N-(1-methylethyl)-3,4-dichloro-benzenesulfonamide N-(3-Chloropropyl)-N-isopropyl-3,4-dichlorobenzenesulfonamide, prepared by reacting 3,4-dichlorobenzenesulfonyl chloride with 3-hydroxypropylamine followed by N-alkylation with 2-bromopropane and displacement of the hydroxyl group by chlorine, (13.94 g), N—CH$_3$ homoveratrylamine (8.23 g), K$_2$CO$_3$ (2.90 g) and Cs$_2$CO$_3$ (7.39 g) in xylene (300 mL) was heated and stirred for 5 days. The reaction was cooled, filtered and stripped to provide a partially solid crude product which was stirred with diethyl ether, filtered and the filtrate stripped to provide 17.11 g. This material was chromatographed on dry-column silica gel (500 g) using ethyl acetate to provide the product which was recrystallized from diethyl ether-hexane to give the impure product (3.95 g) (m.p. 62°–64° C.). A second recrystallization from diethyl ether-hexane provided pure product (3.57 g, m.p. 65°–66° C.).

Analysis for: C$_{23}$H$_{32}$N$_2$Cl$_2$O$_4$S: Calculated: C, 54.86; H, 6.41; N, 5.56. Found: C, 54.91; H, 6.20; N, 5.49.
C.L.=0%.

EXAMPLE 10

N-(3,4-Dichlorophenyl)-3-[[2-(3,4-dimethoxyphenyl)ethyl]methylamino]-N-(1-methylethyl)-1-propanesulfonamide Following the procedures of the preceding examples with the exception that 3,4-dichloroaniline was employed as an initial reactant, N-(3,4-dichlorophenyl)-3-[[2-(3,4-dimethoxyphenyl)ethyl]methylamino]-1-propanesulfonamide was obtained, 4.23 g in dry DMF (40 mL) was treated with 6% NaH/mineral oil (0.267 g) and stirred for one hour. An appropriate amount of 2-bromopropane was added and the reaction was heated at Variac setting 25 overnight. The reaction was stripped to provide 6.13 g of a crude gum. The crude gum was dissolved in methylene chloride, washed with aqueous sodium bicarbonate, and the organic layer stripped. Chromatography provided the pure product (1.49 g) as a gum.

Analysis for: C$_{23}$H$_{32}$N$_2$O$_4$SCl$_2$: Calculated: C, 54.87; H, 6.41; N, 5.56. Found: C, 54.74; H, 6.44; N, 5.43.
C.L.=40%.

EXAMPLE 11

N-(3,4,5-Trimethoxyphenyl)-3-[[1-(3,4,5-trimethoxyphenyl)ethyl]amino]-1-propanesulfonamide 3-Amino-N-(3,4,5-trimethoxyphenyl)-1-propanesulfonamide was prepared from 3-chloro-N-(3,4,5-trimethoxyphenyl)-1-propanesulfonamide. This material (3.04 g, 0.01 mol) and 3,4,5-trimethoxyphenyl acetone (2.10 g, 0.01 mol) was dissolved in absolute methanol (50 mL) containing platinum oxide (0.40 g) and shaken at 50 psi of hydrogen for 16 hours. After filtration and removal of solvent the residue was chromatographed on dry-column silica gel with 5% methanol-ethyl acetate to provide the product (2.47 g) as a partial ethyl acetate solvate.

Analysis for: C$_{23}$H$_{34}$N$_2$O$_8$S.0.5C$_4$H$_8$O$_2$: Calculated: C, 55.23; H, 7.23; N, 5.15. Found: C, 54.82; H, 6.74; N, 5.29.
C.L.=40%.

EXAMPLE 12

3-[[(3,4-Dimethoxyphenyl)methyl]methylamino]-N-[3-(trifluoromethyl)phenyl]propanesulfonamide The title compound was prepared by reaction of 3-chloro-N-3-(trifluoromethyl)phenyl-propanesulfonamide with N-methyl-3,4-dimethoxybenzylamine in xylene as in previous examples.

Analysis for: C$_{20}$H$_{25}$N$_2$O$_4$SF$_3$: Calculated: C, 53.80; H, 5.64; N, 6.27. Found: C, 53.34; H, 5.62; N, 6.04.
C.L.=40%.

EXAMPLE 13

N-[2-[[2-(3,4-Dimethoxyphenyl)ethyl]methylamino]ethyl]-N-(1-methylethyl)-3,4-dichlorobenzenesulfonamide The title compound was prepared by reaction of N-β-chloroethyl-N-(1-methylethyl)-3,4-dichlorobenzenesulfonamide with N-methylhomoveratrylamine in xylene containing inorganic carbonate acid scavengers by heating for five days.

Analysis for: $C_{22}H_{30}N_2Cl_2O_4S$: Calculated: C, 53.99; H, 6.18; N, 5.72. Found: C, 53.94; H, 6.12; N, 5.74. C.L.=0%.

EXAMPLE 14

N-[3-[[2-(3,4-dimethoxyphenyl)ethyl]methylamino]propyl]-N-(1-methylethyl)-2,3,4-trimethoxy-benzene sulfonamide 2,3,4-Trimethoxybenzene sulfonyl chloride (20.4 g, 0.765 m) in methylene chloride (100 ml) was added dropwise to 3-aminopropanol (17.2 g) in methylene chloride (300 ml). After stirring overnight the reaction was washed with dilute aqueous HCl, dried and stripped to provide a solid. Trituration with diethyl ether provided the product N-(3-hydroxypropyl)-2,3,4-trimethoxy-benzenesulfonamide, m.p. 95°–97° C.

Analysis for: $C_{12}H_{19}NO_6S$: Calculated: C, 47.20; H, 6.27; N, 4.57. Found: C, 46.89; H, 6.16; N, 4.57.

The product of the preceding paragraph (17.79 g, 0.58 m) in dry dimethylformamide (100 ml) was treated with 60% NaH/mineral oil (2.31 g, 0.058 m) and then 2-bromopropane (2.31 g, 0.058 m) and heated with stirring overnight. Chromatography indicated only 50% reaction. Therefore the crude product was retreated using the same quantities to provide a crude product (23.84 g). Chromatography provided N-isopropyl-N-(3-hydroxypropyl)-2,3,4-trimethoxybenzenesulfonamide (10.92 g) containing a trace of ethyl acetate.

The product of the preceding paragraph was oxidized to an aldehyde by use of the $CrO_3$/pyridine reagent, prepared from $CrO_3$ (18.84 g), pyridine (29.79 g) in methylene chloride (500 ml). The aldehyde was isolated as a dark gum (7.70 g) and was used directly below.

N-isopropyl-N-(3-oxopropyl)-2,3,4-trimethoxybenzenesulfonamide prepared in the previous paragraph (7.50 g, 0.0384 m), N-methyl-homoveratrylamine (6.83 g, 0.350 m) in absolute ethanol (100 ml) containing $PtO_2$ (0.5 g) was shaken under hydrogen all day. The crude product (8.01 g) obtained from this procedure after chromatography gave the pure title compound, a white gum (5.71 g).

Analysis for: $C_{20}H_{40}N_2O_7S$: Calculated: C, 59.52; H, 7.68; N, 5.34. Found: C, 59.29; H, 7.59; N, 5.20.

P.R.=80%.

C.L.=0%.

What is claimed is:

1. A compound which is N-[3-[[2-(3,4-dimethoxyphenyl)ethyl]methylamino]propyl]-N-(1-methylethyl)-2,3,4-trimethoxy-benzenesulfonamide or a pharmaceutically acceptable salt thereof.

* * * * *